(12) United States Patent
Bernstein

(10) Patent No.: US 6,476,077 B1
(45) Date of Patent: Nov. 5, 2002

(54) N-(2-PHENYL-4-AMINO-BUTYL)-1-NAPHTHAMIDES AS NEUROKININ-1 RECEPTOR ANTAGONISTS

(75) Inventor: Peter Robert Bernstein, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 09/937,981

(22) PCT Filed: Apr. 3, 2000

(86) PCT No.: PCT/GB00/01252

§ 371 (c)(1),
(2), (4) Date: Oct. 2, 2001

(87) PCT Pub. No.: WO00/59873

PCT Pub. Date: Oct. 12, 2000

(30) Foreign Application Priority Data

Apr. 6, 1999 (GB) .................................. 9907571

(51) Int. Cl.⁷ ..................... C07C 255/52; A61K 31/165
(52) U.S. Cl. ...................... 514/620; 558/393
(58) Field of Search ................ 544/163, 162, 544/106; 514/237.8, 231.2, 620; 558/393

(56) References Cited

U.S. PATENT DOCUMENTS 5,824,678 A  * 10/1998  Harrison et al. ......... 514/237.8

FOREIGN PATENT DOCUMENTS

| EP | 0 428 434 A | 5/1991 |
| WO | WOX 94 29309 A | 12/1994 |
| WO | WO 98 25617 A | 6/1998 |
| WO | WO 00/59873 | * 10/2000 |

* cited by examiner

Primary Examiner—Joseph K. McKane
Assistant Examiner—Golam M. M. Shameem
(74) Attorney, Agent, or Firm—Kenneth F. Mitchell

(57) ABSTRACT

A compound having the general formula (I): $R^1R^2N-CH_2CH_2-CHAr^1-CH_2-NR^3-CO-R^4$ wherein: $R^1$ is hydrogen, $C_{1-6}$ alkyl, $C_{2-6}$ alkenyl, aryl, $C_{1-6}$ alkanoyl $C_{1-6}$ alkoxycarbonyl or arylcarbonyl; any of such groups being optionally substituted; $R^2$ is hydrogen or $C_{1-6}$ alkyl; or $R^1$ or $R^2$ are joined to form an optionally substituted morpholino ring; $Ar^1$ is phenyl mono- or di-substituted by halo; $R^3$ is hydrogen or $C_{1-6}$ alkyl; $R^4$ is optionally substituted naphth-1-yl; or pharmaceutically acceptable salts thereof. These compounds antagonize the pharmacological actions of the endogenous neuropeptide tachykinins, particularly the neurokinin 1 (NK1) receptor.

11 Claims, No Drawings

N-(2-PHENYL-4-AMINO-BUTYL)-1-NAPHTHAMIDES AS NEUROKININ-1 RECEPTOR ANTAGONISTS

This application is a 371 of PCT/GB00/01252 Apr. 03, 2000.

BACKGROUND

The mammalian neurokinins comprise a class of peptide neurotransmitters which are found in the peripheral and central nervous systems. The three principal neurokinins are Substance P(SP), Neurokinin A(NKA) and Neurokinin B(NKB). There are also N-terminally extended forms of at least NKA. At least three receptor types are known for the three principal neurokinins. Based upon their relative selectivities favoring the neurokinin agonists SP, NKA and NKB, the receptors are classified as neurokinin 1 ($NK_1$), neurokinin 2 ($NK_2$) and neurokinin 3 ($NK_3$) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation, increased mucus secretion and activation of mast cells. Thus, the tachykinins are implicated in the pathophysiology and airway hyperresponsiveness observed in asthmatics; and blockade of the action of released tachykinins may be useful in the treatment of asthma and related conditions.

SUMMARY OF THE INVENTION

This invention relates to naphthalenecarboxamide compounds N-substituted by an aminobutyl group, to pharmaceutical compositions containing such compounds, as well as to their uses and processes for their preparation. These compounds antagonize the pharmacological actions of the endogenous neuropeptide tachykinins known as neurokinins, particularly at the neurokinin 1 (NK1) receptor. These compounds are useful whenever such antagonism is desired. Thus, such compounds are of value in the treatment of those diseases in which Substance P is implicated, for example, in the treatment of asthma, anxiety, depression, emesis and related conditions.

The N-substituted naphthalenecarboxamide compounds of the present invention show a high degree of NK1 receptor antagonist activity.

DETAILED DESCRIPTION

Accordingly the present invention provides the compounds of the formula (I):

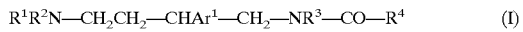

$$R^1R^2N—CH_2CH_2—CHAr^1—CH_2—NR^3—CO—R^4 \quad (I)$$

wherein:
$R^1$ is hydrogen, $C_{1-6}$alkyl, $C_{2-6}$alkenyl, aryl, $C_{1-6}$alkanoyl, $C_{1-6}$alkoxycarbonyl or arylcarbonyl;
any of such groups being optionally substituted;
$R^2$ is hydrogen or $C_{1-6}$alkyl; or
$R^1$ or $R^2$ are joined to form an optionally substituted morpholino ring;

$Ar^1$ is phenyl mono- or di-substituted by halo;
$R^3$ is hydrogen or $C_{1-6}$alkyl;
$R^4$ is optionally substituted naphth-1-yl;
and pharmaceutically acceptable salts thereof.

When $R^1$ is optionally substituted $C_{2-6}$alkyl (for example ethyl or propyl), $C_{2-6}$alkenyl (for example propenyl), $C_{1-6}$alkoxycarbonyl (for example methoxycarbonyl or ethoxycarbonyl) and $C_{1-6}$alkanoyl (for example acetyl or propionyl), suitable substituents include halo for example chloro, bromo or fluoro; nitro; cyano; hydroxy; $C_{1-6}$alkoxy for example methoxy or ethoxy; amino; $C_{1-6}$alkylamino for example methylamino or ethylamino; di-$C_{1-6}$alkylamino for example dimethylamino; trifluoromethyl; carboxy; carbamoyl ($NH_2CO$—); $C_{1-6}$alkylcarbamoyl for example methylcarbamoyl or ethylcarbamoyl; di-$C_{1-6}$alkylcarbamoyl for example dimethyl-carbamoyl; $C_{1-6}$alkanoyl for example acetyl; mercapto; $C_{1-6}$alkylthio for example methylthio or ethylthio; $C_{1-6}$alkylsulphinyl for example methylsulphinyl or ethylsulphinyl; $C_{1-6}$alkylsulphonyl for example methylsulphonyl or ethylsulphonyl; sulphamoyl; $C_{1-6}$alkoxycarbonyl for example methoxycarbonyl or ethoxycarbonyl; $C_{3-8}$cycloalkyl for example cyclopropyl, cyclopentyl or cyclohexyl; cyclobutyl, aryl; or heteroaryl.

When $R^1$ is substituted methyl, suitable substituents are $C_{3-8}$ cycloalkyl for example cyclopropyl, cyclobutyl, cyclopentyl or cyclohexyl; aryl; or heteroaryl.

When $R^1$ is substituted aryl or arylcarbonyl (or when $R^1$ and $R^2$ together with the nitrogen atom to which they are joined form a morpholino ring) suitable substituents include those substituents mentioned hereinabove (for other values of $R^1$), as well as $C_{1-6}$alkyl for example methyl or ethyl, $C_{2-6}$alkenyl for example allyl or vinyl; or $C_{2-6}$alkynyl for example ethynyl.

"Aryl" in the terms "aryl" and "arylcarbonyl" means phenyl and naphthyl.

Preferably $R^1$ is hydrogen, $C_{1-6}$alkyl optionally substituted by phenyl, $C_{2-6}$alkenyl, phenyl or benzoyl.

In particular $R^1$ is hydrogen, methyl, ethyl, n-propyl, isopropyl, propen-2-yl, phenyl or benzoyl.

Preferably $R^2$ is hydrogen or methyl.

In a particularly preferred aspect $R^1$ is methyl or ethyl and $R^2$ is hydrogen or methyl, for example $R^1R^2N$— is methylamino.

In another preferred aspect $R^1$ and $R^2$ together with the nitrogen atom to which they are attached form a morpholino ring.

Favourably $Ar^1$ is phenyl di-substituted by chloro, for example $Ar^1$ is 3,4-dichlorophenyl.

$R^3$ is hydrogen or $C_{1-6}$alkyl for example methyl, ethyl or n-propyl. Preferably $R^3$ is methyl.

$R^4$ is optionally substituted naphth-1-yl. Suitable substituents, which are optional, for the naphth-1-yl group include hydroxy; cyano; nitro; trifluoromethoxy; trifluoromethyl; $C_{1-6}$alkylsulfonyl for example methylsulphonyl; halo for example chloro, bromo, fluoro or iodo; $C_{1-6}$alkoxy for example methoxy, ethoxy or propoxy; methylenedioxy (—$OCH_2O$—), $C_{1-6}$alkyl for example methyl or ethyl; $C_{2-6}$alkenyl for example ethenyl, prop-1-enyl or prop-2-enyl; $C_{2-6}$alkynyl for example ethynyl; carboxy, $C_{1-6}$alkoxycarbonyl for example methoxycarbonyl; carbamoyl; $C_{1-6}$alkylcarbamoyl for example methylcarbamoyl or ethylcarbamoyl; di-$C_{1-6}$alkylcarbamoyl for example di-methylcarbamoyl; $C_{1-6}$alkanoyl for example acetyl or propionyl; $C_{1-6}$alkanoylamino for example acetylamino or propionylamino; aminosulfonyl; and $C_{1-6}$alkyl for example methyl substituted by any of the hereinabove substituents.

Favourably the naphth-1-yl group is unsubstituted or is substituted by up to three substituents. Preferred substituents for the naphth-1-yl group include cyano; nitro; $C_{1-6}$alkylsulfonyl for example methylsulphonyl; halo for example chloro, bromo, fluoro or iodo; $C_{1-6}$alkoxy for example methoxy, ethoxy, n-propoxy or isopropoxy; methylenedioxy (—OCH$_2$O—); $C_{1-6}$alkyl for example methyl or ethyl; $C_{2-6}$alkenyl for example prop-2-enyl; $C_{2-6}$alkynyl for example ethynyl; carboxy, carbamoyl; $C_{1-6}$alkyl-carbamoyl for example methylcarbamoyl; di-$C_{1-6}$alkylcarbamoyl for example di-methylcarbamoyl; $C_{1-6}$alkanoyl for example acetyl; $C_{1-6}$alkanoylamino for example acetylamino; aminosulfonyl; and cyano $C_{1-6}$alkyl for example cyanomethyl.

More preferred substitutents for the naphth-1-yl group are cyano, methoxy, ethoxy, isopropoxy, fluoro, bromo, chloro, iodo, nitro, cyanomethyl, carboxy, carbamoyl, ethynyl, methyl, ethyl, dimethylcarbamoyl, methylsulfonyl, aminosulfonyl, prop-2-enyl, acetyl and acetylamino.

In particular the naphth-1-yl group may be substituted by up to two substituents selected from cyano, methoxy, ethyl, fluoro and nitro. A particularly preferred substitution pattern for the naphth-1-yl group is 3-cyano. A further particularly preferred substitution pattern is 3-cyano, 2-methoxy. Another particularly preferred substitution pattern is 2,3-dimethoxy. Another particularly preferred substitution pattern is 3-cyano, 2-ethyl.

The compounds of the present invention possess a chiral centre, at —CHAr$^1$— and possibly in the optional substituents. The present invention covers all isomers, diastereoisomers and mixtures thereof that antagonise NK1 receptors.

The preferred configuration at —CHAr$^1$— is shown in formula (Ia) hereinbelow:

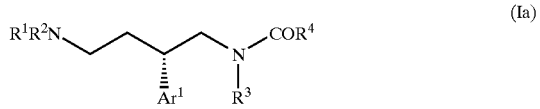

(Ia)

Thus a preferred class of compounds of the present invention is that of the formula (Ia) wherein R$^1$ is hydrogen, methyl or ethyl; R$^2$ is hydrogen or methyl; R$^3$ is methyl; Ar$^1$ is 3,4-dichlorophenyl; and R$^4$ is napth-1-yl optionally substituted by up to two substituents selected from cyano, methoxy, ethyl, fluoro and nitro.

Particular compounds of the invention are those of the Examples.

Pharmaceutically acceptable salts of the compounds of the formula (I) include those made with inorganic or organic acids which afford a physiologically acceptable anion, such as with, for example, hydrochloric, hydrobromic, sulfuric, phosphoric, methanesulfonic, sulfamic, para-toluenesulfonic, acetic, citric, lactic, tartaric, malonic, fumaric, ethanesulfonic, benzenesulfonic, cyclohexylsulfamic, salicyclic and quinic acids.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation or insufflation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to herein.

The pharmaceutical compositions of this invention will normally be administered to humans so that, for example, a daily dose of 0.01 to 25 mg/kg body weight (and preferably of 0.1 to 5 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt thereof. In another example, for administration by inhalation, a compound of the formula (I) or a pharmaceutically acceptable salt thereof may be administered in a daily dosage range of 5 to 100 mg, in a single dose or divided into two to four daily doses. In a further example, for administration by intravenous or intramuscular injection or infusion, a sterile solution or suspension containing up to 10% w/w (and typically 5% w/w) of a compound of the formula (I) or a pharmaceutically acceptable salt thereof may be used.

Therefore in a further aspect, the present invention provides a compound of the formula (I) or a pharmaceutically acceptable salt thereof for use in a method of therapeutic treatment of the human or animal body.

In yet a further aspect the present invention provides a method of treating a disease condition wherein antagonism of the NK1 receptor is beneficial which comprises administering to a warm-blooded animal an effective amount of a compound of the formula (I) or a pharmaceutically acceptable salt thereof. The present invention also provides the use of a compound of the formula (I) or a pharmaceutically acceptable salt thereof in the preparation of a medicament for use in a disease condition wherein antagonism of the NK1 receptor is beneficial.

The compounds of the formula (I) and their pharmaceutically acceptable salts may be made by processes as described and exemplified herein and by processes similar thereto and by processes known in the chemical art. If not commercially available, starting materials for these processes may be made by procedures which are selected from the chemical art using techniques which are similar or analogous to the synthesis of known compounds.

In another aspect the present invention provides a process for preparing a compound of the formula (I) or a pharmaceutically acceptable salt thereof which process comprises:
a) reacting a compound of the formula (III):

OHC—CH$_2$—CHAr$^1$—CH$_2$—NR$^3$—COR$^4$ (III)

wherein Ar$^1$, R$^3$ and R$^4$ are as hereinbefore defined with a compound of the formula R$^1$R$^2$NH; or b) reacting a compound of the formula (IV):

$$R^1R^2N-CH_2-CH_2-CHAr^1-CH_2-NHR^3 \quad (IV)$$

wherein $R^1$, $R^2$, $R^3$ and $Ar^1$ are as hereinbefore defined with a compound of the formula L—CO—$R^4$ wherein L is a leaving group;
wherein any functional group is protected, if necessary, and
i) removing any protecting group;
ii) optionally converting a compound of the formula (I) into another compound of the formula (I);
iii) optionally forming a pharmaceutically acceptable salt.

Protecting groups may in general be chosen from any of the groups described in the literature or known to the skilled chemist as appropriate for the protection of the group in question, and may be introduced and removed by conventional methods; see for example Protecting Groups in Organic Chemistry; Theodora W. Greene. Methods of removal are chosen so as to effect removal of the protecting group with minimum disturbance of groups elsewhere in the molecule.

It will also be appreciated that certain of the various optional substituents in the compounds of the formula (I) may be introduced by standard aromatic substitution reactions or generated by conventional functional group modifications either prior to or immediately following the processes described hereinabove. The reagents and reaction conditions for such procedures are well known in the chemical art.

Pharmaceutically acceptable salts may be prepared from the corresponding acid in conventional manner. Non-pharmaceutically acceptable salts may be useful as intermediates and as such are another aspect of the present invention.

It is well known in the art how to prepare optically-active forms (for example, by resolution of the racemic form or by synthesis from optically-active starting materials) and how to determine the NK1 antagonist properties by the standard tests known in the art and those described hereinafter.

The compounds of the formulae (E) and $R^1R^2NH$ are reacted under conditions of reductive amination. The reaction is typically performed at a non-extreme temperature, for example 0–100° C., more suitably at ambient temperature, in a substantially inert solvent for example dichloromethane or methanol. Typical reducing agents include borohydrides such as sodium cyanoborohydride. The compounds of the formula $R^1R^2NH$ are known or may be prepared in conventional manner. The compounds of the formula (III) may be prepared from the corresponding alcohol, which itself may be prepared by N-acylation of the corresponding substituted hydroxybutylamine.

The compounds of the formula (IV) and LCOR$^4$ are reacted under conventional acylation conditions wherein LCOR$^4$ is an acid or activated acid derivative such as an acid chloride. The compounds of the formula (IV) may be prepared by reacting a compound of the formula (V):

$$OHC-CH_2-CHAr^1-CH_2NHR^3 \quad (V)$$

wherein $Ar^1$ and $R^3$ are as hereinbefore defined, with $R^1R^2NH$ under reductive amination conditions, with functional groups being protected as necessary. For example, when it is desired to prepare a compound of the formula (IV) when $R^3$ is hydrogen, the —NHR$^3$ function of the compound of the formula (V) may be protected as a phthalimido group, removal conventionally such as by hydrazinolysis. The compounds of the formula (V) are known or may be prepared in conventional manner for example from the corresponding substituted hydroxybutylamine.

The compounds of the formula (I) may be converted to other compounds of the formula (I), for example a compound of the formula (I) wherein $R^1$ is hydrogen may be acylated in conventional manner to form the corresponding compound wherein $R^1$ is arylcarbonyl or alkanoylcarbonyl.

The following biological test methods, data and Examples serve to illustrate and further describe the invention.

The utility of a compound of the invention or a pharmaceutically acceptable salt thereof (hereinafter, collectively referred to as a "Compound") may be demonstrated by standard tests and clinical studies, including those disclosed in the publications described below.

SP Receptor Binding Assay (Test A)

The ability of a Compound of the invention to antagonize the binding of SP at the NK1 receptor may be demonstrated using an assay using the human NK1 receptor expressed in Mouse Erythroleukemia (MEL) cells. The human NK1 receptor was isolated and characterized as described in: B. Hopkins, et al. "Isolation and characterization of the human lung NK1 receptor cDNA" *Biochem. Biophys. Res. Comm.,* 1991, 180, 1110–1117; and the NK1 receptor was expressed in Mouse Erythroleukemia (MEL) cells using a procedure similar to that described in Aharony, D., et al. "Isolation and Pharmacological Characterization of a Hamster Neurokinin A Receptor cDNA" *Molecular Pharmacology,* 1994, 45, 9–19.

Rabbit Pulmonary Artery: NK1 in vitro functional assay (Test C)

The ability of a Compound of the invention to antagonize the action of the agonist Ac-[Arg$^6$, Sar$^9$, Met(O2)$^{11}$] Substance P (6–11), ASMSP, in a pulmonary tissue may be demonstrated according to published methods; J. Pharmacol. Exp. Ther. 1993, 267, 1168; Buckner C K, Liberati N, Dea D, Lengel D, Stinson-Fisher C, Campbell J, Miller S, Shenvi A, Krell R D.

Male New Zealand white rabbits are euthanized via i.v. injection into an ear vein with 60 mg/kg Nembutal (50 mg/ml). Preceding the Nembutal into the vein is Heparin (1000 units/ml) at 0.0025 ml/kg for anticoagulant purposes. The chest cavity is opened from the top of the rib cage to the sternum and the heart, lungs and part of the trachea are removed. The pulmonary arteries are isolated from the rest of the tissues and cut in half to serve as pairs.

The segments are suspended between stainless steel stirrups, so as not to remove any of the endothelium, and placed in water-jacketed (37.0° C.) tissue baths containing physiological salt solution of the following composition (mM): NaCl, 118.0; KCl, 4.7; CaCl$_2$, 1.8; MgCl$_2$, 0.54; NaH$_2$PO$_4$, 1.0; NaHCO$_3$, 25.0; glucose, 11.0; indomethacin, 0.005(to inhibit cyclooxygenase); and dl-Propranolol, 0.001 (to block β receptors); gassed continuously with 95% O$_2$–5% CO$_2$. Responses are measured on a Grass polygraph via Grass FT-03 transducers and the electrical signals (data) acquired using a Mi$^2$ software/hardware system for subsequent conversion to measures of relaxation.

Initial tension placed on each tissue is 2 grams, which is maintained throughout the 1.0 hour equilibration period. Tissues are washed with the physiological salt solution at 15 minute intervals. At the 30 and 45 minute wash the following treatments are added: 1×10$^{-6}$M Thiorphan (to block E.C.3.4.24.11), 3×10$^{-8}$M (S)-N-[2-(3,4-Dichlorophenyl)-4-[4-(2-oxoperhydropyrimidin-1-yl)piperidino]butyl]-N-methylbenzamide (to block NK2 receptors), and the given concentration of the Compound being tested. At the end of the 1.0 hour equilibration, 1×10$^{-6}$M L-Phenylephrine hydrochloride is added for 1.0 hour. At the end of the 1.0 hour, a dose relaxation curve to ASMSP is done. Each tissue is treated as a individual and is considered finished when it fails to relax further for 2 consecutive doses. When this section of the protocol is complete, $1\times10^{-3}$M Papaverine is added for maximum relaxation.

For non-competitive antagonists, the percent inhibition of relaxation is determined at a given concentration of the antagonist. Percent inhibition is determined when a tested Compound produces a statistically significant (p<0.05) reduction of the total relaxation which is calculated using the total relaxation as a percent of the control value. Potencies of competitive Compounds are determined by calculating the apparent dissociation constants ($K_B$) for each concentration tested using the standard equation:

$$K_B=[\text{antagonist}]/(\text{dose ratio}-1)$$

where dose ratio=antilog[(agonist –log molar $EC_{50}$ without Compound)–(–log molar $EC_{50}$ with Compound)]. The $K_B$ values may be converted to the negative logarithms and expressed as –log molar $K_B$(i.e. $pK_B$). For this evaluation, complete concentration-response curves for agonist obtained in the absence and presence of the Compound tested using paired pulmonary artery rings. The potency of the agonist is determined at 50% of its own maximum relaxation in each curve. The $EC_{50}$ values are converted to negative logarithms and expressed as –log molar $EC_{50}$.

$NK_1$ in vivo Functional Assay (Test E)

The activity of a compound as an antagonist of $NK_1$, receptors also may be demonstrated in vivo in laboratory animals as described in: Buckner et al. "Differential Blockade by Tachykinin $NK_1$ and $NK_2$ Receptor Antagonists of Bronchoconstriction Induced by Direct-Acting Agonists and the Indirect-Acting Mimetics Capsaicin, Serotonin and 2-Methyl-Serotonin in the Anesthetized Guinea Pig." *J. Pharm. Exp. Ther.,* 1993, Vol 267(3), pp1168–1175.

Results of testing of representative compounds of the present invention by the above methods are presented in the Table I:

TABLE 1

| Example | $NK_1$ pKb (Test C) |
|---------|---------------------|
| 4       | 8.3                 |
| 6       | 8.7                 |

Clinical Studies

Clinical studies to demonstrate the efficacy of a Compound of the invention may be carried out using standard methods.

The Tests provide evidence of general antagonism of SP. SP has been implicated in the pathology of numerous diseases including: rheumatoid arthritis, Alzheimer's disease, cancer, schizophrenia, oedema, allergic rhinitis, inflammation, pain, gastrointestinal-hypermotility, gastric asthma, gastroesphageal reflux, anxiety, emesis, Huntington's Disease, psychoses including depression, hypertension, migraine and urticaria.

Accordingly, one feature of the invention is the use of a compound of formula (I) or a pharmaceutically acceptable salt thereof in the treatment of a disease in a human or other mammal in need thereof in which SP is implicated and antagonism of its action is desired.

There is a possible role for Substance P antagonists in the treatment of depression. Accordingly another feature of the invention is the use of a compound of formula (I) or a pharmaceutically acceptable salt thereof in the treatment of depression in a human or other mammal in need thereof.

Because of the range of effects attributable to the actions of SP, compounds which are capable of blocking their actions may also be useful as tools for further evaluating the biological actions of other neurotransmitters in the Tachykinin family. As a result, another feature of the invention is provided by the use of a compound of Formula I or a salt thereof as a pharmacological standard for the development and standardization of new disease models or assays for use in developing new therapeutic agents for treating diseases in which SP are implicated or for assays for their diagnosis. The invention is illustrated by the following non-limiting examples, in which, where applicable and unless stated otherwise:

(i) operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) melting points are uncorrected;

(iv) final products had satisfactory proton nuclear magnetic resonance (NMR) spectra;

(v) Mass spectra (MS) were run using an automated system with atmospheric pressure chemical ionization (APCI). Generally, only spectra where parent masses are observed are reported.

Abbreviations: CO, carbon monoxide; DCM; methylene chloride, DMF; N;N-dimethylformamide, DMSO; dimethyl sulfoxide, $Et_2O$; diethyl ether, EtOAc; ethyl acetate,h; hour (s), min; minutes, NMR; nuclear magnetic resonance, psi; pounds per square inch, THF; tetrahydrofuran.

Standard acylation refers to the typical procedure in which an acid chloride (1–1.2 equivalents) is added to a stirred solution of an amine (1–1.2 equivalents) and triethylamine (2 equivalents) in DCM. After 1–16 h the reaction is optionally concentrated, dissolved in DCM, and washed with saturated sodium bicarbonate and then purified by chromatography.

Standard reductive amination refers to the typical procedure in which a solution of an amine (1–1.2 equivalents), an aldehyde (1–1.2 equivalents) and acetic acid (2 equivalents) are stirred in methanol for 5 to 60 minutes before adding $NaBH_3CN$ (1.7 equivalents). After 1–16 h the reaction is optionally concentrated, dissolved in DCM, and washed with saturated sodium bicarbonate and then purified by chromatography.

Final compounds were converted to the citrate salt. The free base was combined with citric acid (1.0 equivalents) in methanol, concentrated under reduced pressure and dried under vacuum (25–50° C.).

EXAMPLE 1

N-[(S)-2-(3,4-Dichlorophenyl)-4-(phenylamino) butyl]-N-methyl-2-methoxy-3-cyano-1-naphthamide N-[(S)-2-(3,4-Dichlorophenyl)-4-oxobutyl]-N-methyl-2-methoxy-3-cyano-1-naphthamide was reacted with aniline under standard reductive amination conditions to give the title compound which was converted to the citrate salt. $^1$H NMR(300 MHz, DMSO-$d_6$) δ8.64–8.61 (m), 8.07–7.98 (m), 7.79–7.55 (m), 7.51–7.47 (m), 7.37–7.32 (t), 7.08–7.00 (m), 6.53–6.49 (m), 6.31–6.28 (d), 4.60–4.50 (t), 4.07–3.96 (m), 3.92 (s), 3.90–3.78 (m), 3.86 (s), 3.45–3.11 (m), 3.00–2.88 (m), 2.79 (s), 2.73 (s), 2.68 (s), 2.56–2.44 (m), 2.03–1.88 (m); MS APCI, m/z=532 ($M^+$).

N-[(S)-2-(3,4-Dichlorophenyl)-4-oxobutyl]-N-methyl-2-methoxy-3-cyano-1-naphthamide was prepared as follows:

(a) 3-Hydroxy-4-iodo-2-naphthoic Acid

A mixture of NaOH (2.12 g) in methanol (100 mL) was stirred until the solution was homogeneous. Sodium iodide (3.98 g) and 3-hydroxy-2-naphthoic acid (5.00 g) were added and allowed to stir for 30 min. The resulting suspension was cooled to 0° C. and a 5.25% (w/v) aqueous solution of sodium hypochlorite was added dropwise and stirring continued for 1 h. Saturated sodium thiosulfate (25 mL) was added and after 5 min the solution was acidified to pH 2 by addition of 6N HCl resulting in the formation of a yellow precipitate which was filtered and washed with water (50 mL). The precipitate was transferred to a round-bottomed flask, dissolved in methanol (70 mL) and toluene (100 mL), concentrated, redissolved in methanol (70 mL), concentrated, redissolved again in methanol (70 mL) and toluene (100 mL) and concentrated to afford the product as a yellow solid (6.26 g). MS m/z 313 (M–1). $^1$H NMR (DMSO-$d_6$): δ12.41(broad, 1 H), 8.63 (s,1 H), 8.05–7.97 (m, 2 H), 7.70 (m, 1 H), 7.42 (m, 1H).

(b) Methyl 3-methoxy-4-iodo-2-naphthoate

A solution of 3-hydroxy-4-iodo-2-naphthoic acid (8.0 g), dimethyl sulfate (8.03 g), powdered potassium carbonate (8.80 g), and dry acetone (150 mL) was heated under reflux for 18 h. The solution was cooled to room temperature, triethylamine (15 mL) was added, and stirring continued for 30 min. The solution was filtered through a pad of Celite and washed with dry acetone (50 mL). The filtrate was concentrated to a yellow oil, diluted with EtOAc, and washed successively with 1N HCl (100 mL), saturated aqueous sodium bicarbonate (100 mL), and brine (100 mL). The organic phase was dried (sodium sulfate), filtered, concentrated, and purified by chromatography (0–10% EtOAc in hexanes) to afford the product as a yellow oil (5.53 g). $^1$H NMR (DMSO-$d_6$) δ8.47 (s,1 H), 8.09 (m,2 H), 7.74 (m, 1 H), 7.61 (m, 1 H), 3.94 (s,3 H), 3.87 (s,3 H).

(c) 1-Iodo-2-methoxy-3-cyanonaphthalene

Based on the procedure of Wood, J L; Khatri, N A; Weinreb, S M; Tetrahedron Lett; 51, 4907 (1979), methyl 3-methoxy-4-iodo-2-naphthoate (5.0 g) was suspended in xylenes (100 mL), cooled to 0° C., dimethylaluminum amide solution (approximately 37 mmol) was added and the solution heated under reflux for 2.5 h. The solution was then cooled to 0° C. and acidified to pH 2 by addition of 1N HCl and extracted with EtOAc (3×100 mL). The combined EtOAc extracts were washed with saturated aqueous sodium bicarbonate (150 mL) and brine (150 mL), dried (sodium sulfate), filtered, concentrated, and purified by chromatography (1:1 EtOAc:DCM, then 10–20% EtOAc in DCM) to afford the product as a white solid (3.29 g). $^1$H NMR (DMSO-$d_6$): δ8.69 (s, 1 H), 8.24–8.04 (m, 2 H), 7.91–7.81 (m, 1 H), 7.76–7.65 (m, 1 H), 3.99 (s, 3 H); MS m/z 311 (M+H).

(d) Methyl 2-methoxy-3-cyano-1-naphthoate

Through a suspension of 1-iodo-2-methoxy-3-cyanonaphthalene (0.250 g), Pd(OAc)$_2$ (0.018 g), triethylamine (0.081 g) and methanol (20 mL) was bubbled carbon monoxide for 25 min, then stirred at 70° C. under carbon monoxide (1 atm) for 18 h. The cooled solution was filtered, rinsed with methanol (20 mL) and DCM (20 mL), concentrated, preadsorbed onto silica (1 g) and purified by chromatography (0–10% EtOAc in hexanes) to afford the product as a white solid (0.113 g). $^1$H NMR (DMSO-$d_6$): δ8.78 (s, 1 H), 8.12–8.09 (m, 1 H), 7.84–7.78 (m, 2 H), 7.70–7.63 (m, 1 H), 4.02–4.01 (m, 6 H); IR (cm$^{-1}$): 2228, 1724, 1296, 1236, 1208, 1017.

(e) 2-Methoxy-3-cyano-1-naphthoic Acid

A solution of methyl 2-methoxy-3-cyano-1-naphthoate (0.113 g), LiOH.H$_2$O (0.0196 g), THF (3 mL), water (1 mL) and methanol (1 mL) was stirred overnight at room temperature. The solution was diluted with saturated sodium bicarbonate and extracted with Et$_2$O. The aqueous layer was acidified to pH 2 by addition of 1N HCl and extracted with Et$_2$O. The organic layer was washed with water (30 mL) and brine (40 mL), dried (sodium sulfate), filtered, and concentrated to a white solid. $^1$H NMR (DMSO-$d_6$): δ14.06 (broad, 1 H), 8.08–8.02 (m, 1 H), 7.83–7.76 (m, 2 H), 7.69–7.63 (m, 1 H), 4.02 (s, 3 H); MS m/z: 226 (M–1).

(f) 2-Methoxy-3-cyano-1-naphthoyl Chloride

The carboxylic acid was converted to the corresponding acid chloride by reaction with oxalyl chloride in DCM with a catalytic amount of DMF. After concentrating the reaction mixture to dryness, the acid chloride was used without purification.

(g) N-[2-(S)-(3,4-Dichlorophenyl)-4-hydroxybutyl]-N-methyl-3-cyano-2-methoxy-1-naphthamide A solution of N-[(S)-2-(3,4-Dichlorophenyl)-4-hydroxybutyl]-N-methylamine (Miller, S C; WO 9512577) in DCM was combined with 10% aqueous sodium bicarbonate solution. The mixture was cooled to 0° C. and a solution of 3-cyano-2-methoxy-1-naphthoyl chloride in DCM was added dropwise over 30 min. After stirring overnight at room temperature, the organic phase was concentrated and purified by column chromatography to afford N-[2-(S)-(3,4-dichlorophenyl)-4-hydroxybutyl]-N-methyl-3cyano-2methoxy-1-naphthamide. $^1$H NMR (300 MHz, DMSO-$d_6$) δ9.70–9.64 (m), 8.67–8.57 (m), 8.07–7.97 (m), 7.80 (s), 7.72–7.55 (m), 7.52–7.48 (m), 7.40–7.33 (m), 7.12–7.10 (d), 7.04–7.02 (d), 6.87–6.83 (m), 6.37–6.29 (d), 4.53–4.44 (t), 4.11–4.00 (m), 3.94 (s), 3.92 (s), 3.91–3.73 (m), 3.71 (s), 3.45–3.38 (m), 3.33 (s), 3.14 (s), 2.97–2.95 (d), 2.63 (s), 2.60 (s); MS APCI, m/z=455(M$^+$). This compound was characterized as a mixture of atropoisomers.

(h) N-[2-(S)-(3,4-Dichlorophenyl)-4-oxobutyl]-N-methyl-3-cyano-2-methoxy-1-naphthamide The alcohol from (g) was oxidized using oxalyl chloride and DMSO under standard Swern conditions to afford the aldehyde. $^1$H NMR (300 MHz, DMSO-$d_6$) δ9.70–9.64 (m), 8.67–8.57 (m), 8.07–7.97 (m), 7.80 (s), 7.72–7.55 (m), 7.52–7.48 (m), 7.40–7.33 (m), 7.12–7.10 (d), 7.04–7.02 (d), 6.87–6.83 (m), 6.37–6.29 (d), 4.53–4.44 (t), 4.11–4.00 (m), 3.94 (s), 3.92 (s), 3.91–3.73 (m), 3.71 (s), 3.45–3.38 (m), 3.33 (s), 3.14 (s), 2.97–2.95 (d), 2.63 (s), 2.60 (s); MS APCI, m/z=455 (M$^+$). This compound was characterized as a mixture of atropoisomers.

EXAMPLES 2–6

For examples 2, 3, 4, and 6, N-[(S)-2-(3,4-dichlorophenyl)-4-oxobutyl]-N-methyl-2-methoxy-3-cyano-1-naphthamide was reacted with the appropriate amine under standard reductive amination conditions.

Example 5 was prepared in like manner except that, N-[(S)-2-(3,4-dichlorophenyl)-4-oxobutyl]-N-methyl-2-methoxy-3-cyano-1-naphthamide was replaced with N-[(S)-2-(3,4-dichlorophenyl)-4-oxobutyl]-N-methyl-3-cyano-1-naphthamide. All compounds were converted to the corresponding citrate salts.

EXAMPLE 2

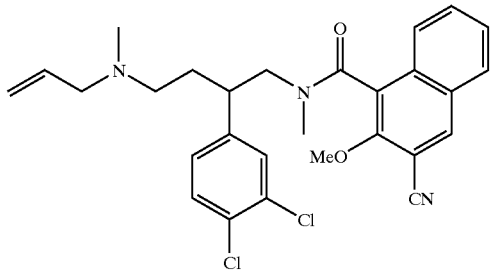

¹H NMR (300 MHz, DMSO-d₆) δ8.65–8.63 (m), 8.12–7.98 (m), 7.77–7.55 (m), 7.51–7.46 (t), 7.39–7.34 (t), 7.07–7.02 (m), 6.89–6.80 (m), 6.32–6.29 (d), 5.87–5.76 (m), 5.39–5.21 (m), 4.55–4.47 (t), 3.94 (s), 3.93–3.77 (m), 3.70 (s), 3.64–3.17 (m), 3.11–2.74 (m), 2.67–2.47 (m), 2.38–2.14 (m), 2.00 (bs), 1.35–1.07 (m); MS APCI, m/z=510 (M⁺).

EXAMPLE 3

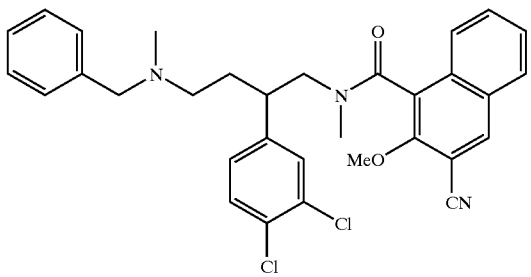

¹H NMR (300 MHz, DMSO-d₆) δ8.65–8.63 (m), 8.08–7.97 (m), 7.71–7.69 (m), 7.67–7.49 (m), 7.40–7.37 (m), 7.31–7.22 (m), 7.03–7.00 (d), 6.89–6.85 (d), 6.77–6.74 (d), 6.31–6.29 (d), 4.53–4.46(t), 4.01–3.96 (m), 3.94 (s), 3.92 (s), 3.88–3.76 (m), 3.68 (s), 3.47–3.16 (m), 3.10 (s), 3.01 (s), 2.70–2.45 (m), 2.34 (bs), 2.06–1.96 (m); MS APCI, m/z=560 (M⁺).

EXAMPLE 4

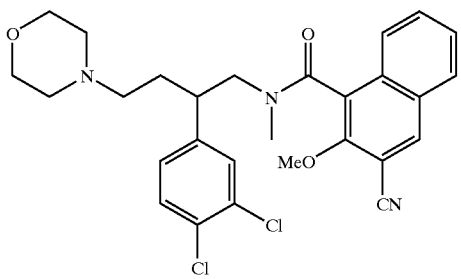

¹H NMR (300 MHz, DMSO-d₆, 373 K) δ8.6–8.7 (m), 7.9–8.1 (m), 7.3–7.8 (m), 6.8–7.1 (m), 6.3 (d), 4.5 (t), 3.0–4.0 (m), 2.6–2.7 (m), 1.8–2.4 (m); MS APCI, m/z=526 (M⁺); analysis calculated for C₂₈H₂₉Cl₂N₃O₃, 1.0 citric acid, 1.0 water, C, 55.44; H, 5.34; N, 5.70; found C, 55.57; H, 5.12; N, 5.65.

EXAMPLE 5

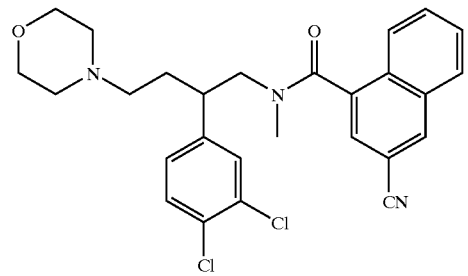

Morpholine is the amine, except N-[2-(S)-(3,4-dichlorophenyl)-4-oxobutyl]-N-methyl-3-cyano-1-naphthamide was used in place of N-[2-(S)-(3,4-dichlorophenyl)-4-oxobutyl]-N-methyl-3-cyano-2-methoxy-1-naphthamide. ¹H NMR (300 MHz, DMSO-d₆, 373 K) δ8.4 (s), 8.0 (d), 7.2–7.7 (m), 3.8 (s), 3.5 (m), 3.2 (s), 2.6–2.8 (m), 2.2–2.4 (m), 1.6–2.0 (m); MS APCI, m/z=496 (M⁺); analysis calculated for C₂₇H₂₇Cl₂N₃O₂, 1.0 citric acid, 1.0 water, C, 56.10; H, 5.28; N, 5.95; found C, 56.40; H, 5.07; N, 5.95.

EXAMPLE 6

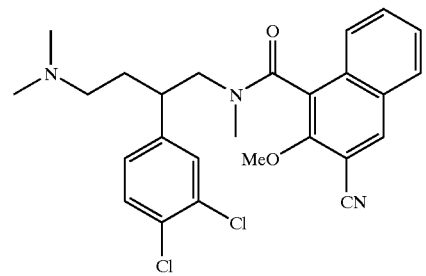

¹H NMR (300 MHz, DMSO-d6) δ8.64 (d), 8.04 (m), 7.79–7.56 (m), 7.49 (d), 7.40–7.32 (m), 7.08 (m), 6.84 (m), 6.32 (d), 4.50 (t), 3.95 (m), 3.89–3.75 (m), 3.71 (s), 3.49 (m), 3.32 (m), 3.14 (m), 3.07 (s), 2.95 (m), 2.64 (s), 2.58 (s), 2.54 (s), 2.50 (s), 2.45 (m), 2.38 (m), 2.18 (m), 2.08–1.98 (m); MS APCI, m/z=484 (M⁺).

For Example 5, the intermediate N-[2-(S)-(3,4-dichlorophenyl)-4-oxobutyl]-N-methyl-3-cyano-1-naphthamide was prepared as follows:

(i) 3-Cyano-1-naphthoyl chloride

Using the procedure of Rule, H G and Thompson, S B; J. Chem. Soc. 1764–1767 (1937), 1,8-naphthalic anhydride was brominated and converted to 3-bromo-1-naphthoic acid. This was esterified to methyl 3-bromo-1-naphthoate according to the following procedure. 3-Bromo-1-naphthoic acid (103.0 g, 410 mmol) was dissolved in DCM (1250 mL) and the solution cooled to 0° C. Oxalyl chloride (67.5 g, 532 mmol) was added in one portion followed by a catalytic amount of DMF (1.5 mL), and the resulting solution allowed to warm to ambient temperature and stir for 4 hours. The mixture was evaporated in vacuo, and the residue concentrated a second time from toluene. The resultant acid chloride was dissolved in methanol (1250 mL) and stirred at ambient temperature for 18 h. The mixture was evaporated in vacuo, and the residue purified by chromatography (eluent: DCM:hexanes 1:3) to provide methyl 3-bromo-1-naphthoate as a white solid (106.9 g, 98%). ¹H-NMR (CDCl₃) δ4.01 (s, 3H, CO₂CH₃); 7.50–7.69 (m, 2H, aromatic); 7.78–7.87 (d, 1H, aromatic); 8.18 (s, 1H, aromatic); 8.25 (s, 1H, aromatic); 8.80–8.94 (d, 1H, aromatic). Using the procedure of Dewar, J S and Grisdale, P J; J. Amer. Chem. Soc., 84, 3541–3546 (1962), methyl-3-bromo-1-naphthoate was converted to methyl 3-cyano-1-naphthoate and then saponified (LiOH) to afford 3-cyano-1-naphthoic acid. 3-Cyano-1-naphthoic acid (15.9 g, 80.6 mmol) was suspended in DCM (4590 mL). To the stirred mixture was added oxalyl chloride (12.8 g, 100 mmol) in one portion followed by a catalytic amount (5 drops) of DMF. The mixture was stirred for 5 hours at room temperature giving a clear solution. The mixture was concentrated in vacuo, and the residue concentrated twice from toluene to provide the crude acid chloride as a light yellow solid (17.4 g, quantitative). ¹H-NMR (300 MHz, d₆ acetone) δ7.86–7.91 (t, 1H, aromatic); 7.98–8.04 (t, 1H, aromatic); 8.28–8.32 (d, 1H, aromatic); 8.66–8.72 (d, 1H, aromatic); 8.80 (s, 1H, aromatic); 8.93 (s, 1H, aromatic).

(ii) N-[(S)-2-(3,4-Dichlorophenyl)-4-hydroxybutyl]-N-methyl-3-cyano-1-naphthamide (S)-2-(3,4-Dichlorophenyl)-4-hydroxybutylamine (20.8 g, 83.8 mmol) was dissolved in DCM (700 mL). To the stirred solution was added 10% aqueous sodium bicarbonate (300 mL), and the mixture cooled to 0° C. A solution of 3-cyano-1-naphthoyl chloride (17.4 g, 80.6 mmol) in DCM (300 mL) was added dropwise over 30 minutes. The mixture was then allowed to warm to ambient temperature and stir for 20 h. The layers were separated, and the aqueous phase washed with DCM (300 mL). The combined organic layers were dried (Na₂SO₄), filtered, and evaporated in vacuo to give a white foam. Purification by chromatography (silica gel; 0–25% acetonitrile in DCM) provided the desired product as a white foam (27.0 g, 78%). ¹H-NMR (DMSO-d₆) δ1.46–1.60 (m, 1H, CH); 1.77–1.91 (m, 3H, CH); 4.3–4.41 (t, 1H, CH); 4.5–4.57 (t, 2H, CH); 6.43 (broad, 1H, OH); 6.8–7.26 (m, 2H, aromatic); 7.44–7.54 (m, 3H, aromatic); 7.57–7.80 (m, 7H, aromatic); 8.04–8.33 (m, 2H, aromatic); 8.61 (s, 1H, aromatic).

(iii) N-[(S)-2-(3,4Dichlorophenyl)-4-oxobutyl]-N-methyl-3-cyano-1-naphthamide

A solution of oxalyl chloride (15.9 g, 125.4 mmol) dissolved in DCM (350 mL) was cooled to −78° C. DMSO (19.6 g, 251 mmol) was added dropwise over 10 minutes while maintaining the temperature of the reaction mixture below −70° C. The mixture was stirred for 30 min at −78° C. A solution of N-[(S)-2-(3,4-dichlorophenyl)-4-hydroxybutyl]-N-methyl-3-cyano-1-naphthamide (26.8 g, 62.7 mmol) was dissolved in DCM (350 mL) and added dropwise over 30 min while maintaining the temperature of the mixture below −70° C. The mixture was allowed to stir for one h at −78° C., then warmed to −50° C. and stirred for another 30 minutes. The mixture was cooled to −78° C. and a solution of triethylamine (25.4 g, 251 mmol) dissolved in DCM (70 mL) was added dropwise over 10 min. The mixture was then allowed to warm gradually to ambient temperature and stir for 20 hours. The mixture was then washed with 0.5N hydrochloric acid (2×250 mL), water (250 mL), and saturated sodium bicarbonate (250 mL). The organic layer was dried (Na₂SO₄), filtered, and concentrated in vacuo. The residue was purified by chromatography (silica gel; 0–20% Et₂O in DCM) to provide the desired product as a light yellow foam (26.0 g, 97%). MS: 425 (M+H). ¹H-NMR (DMSO-d₆) δ2.63 (bs, 3H, NCH₃); 2.99–3.93 (m, 5H, CH); 6.91–7.15 (m, 1H, aromatic); 7.33–7.81 (m, 6H, aromatic); 8.62 (s, 1H, aromatic); 9.45 and 9.73 (singlets, 1H total, CHO).

EXAMPLE 7

The allyl group from the product of Example 2 was removed using Pd(dba)₂ (i.e. bis(dibenzylideneacetone) palladium) in the presence of 2-mercaptobenzoic acid according to the procedure of Lemaire-Andoire et al., Tetr. Lett. 1995, 36, 1267, to give the corresponding methylamine.

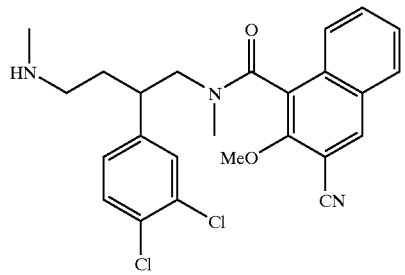

¹H NMR (300 MHz, DMSO-d₆) δ8.66–8.64 (m), 8.08–7.96 (m), 7.80–7.56 (m), 7.51–7.47 (m), 7.40–7.35 (m), 7.07–7.05 (m), 6.85–6.79 (m), 6.35–6.32 (d), 4.54–4.45 (t), 3.95 (s), 3.92 (s), 3.90–3.70 (m), 3.72 (s), 3.50–3.10 (m), 2.86–2.50 (m), 2.44–1.69 (m); MS APCI, m/z=470 (M⁺).

EXAMPLE 8

A solution of the product from Example 7 in DCM was stirred with a 10% solution of sodium carbonate. To this mixture was added a solution of benzoyl chloride. After two hours, the organic layer was separated, washed, and purified by flash chromatography.

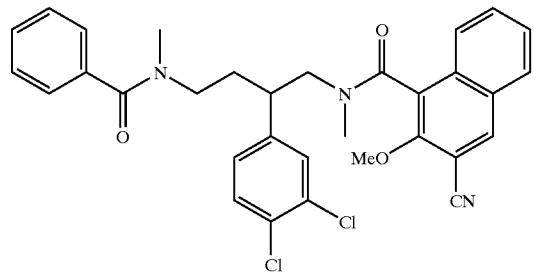

¹H NMR (300 MHz, DMSO-d₆) δ12.26 (br s), 8.63 (d), 8.04 (m), 7.81–7.22 (m), 6.83 (m), 6.32 (m), 5.18 (m), 4.45 (m), 3.93 (s), 3.70 (m), 3.33 (br s), 3.14–2.97 (m), 2.84 (m), 2.05 (br m); MS APCI, m/z 574 (M⁺).

What is claimed is:

1. A compound of the formula (I):

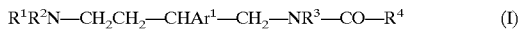

R¹R²N—CH₂CH₂—CHAr¹—CH₂—NR³—CO—R⁴     (I)

wherein:

R¹ is hydrogen, C₁₋₆alkyl, C₂₋₆alkenyl, aryl, C₁₋₆alkanoyl, C₁₋₆alkoxycarbonyl or arylcarbonyl; any of such groups being optionally substituted;

$R^2$ is hydrogen or $C_{1-6}$alkyl;

$Ar^1$ is phenyl mono- or di-substituted by halo;

$R^3$ is hydrogen or $C_{1-6}$alkyl;

$R^4$ is optionally substituted naphth-1-yl; or pharmaceutically acceptable salts thereof.

2. The compound according to claim 1 wherein $R^1$ is hydrogen, $C_{2-6}$alkenyl, phenyl, benzoyl or $C_{1-6}$alkyl optionally substituted by phenyl.

3. The compound according to claim 1 wherein $R^1$ is hydrogen, methyl, ethyl, n-propyl, isopropyl, propen-2-yl, phenyl or benzoyl.

4. The compound according to claim 1 wherein $R^2$ is hydrogen or methyl.

5. The compound according to claim 1 wherein $R^1$ is methyl or ethyl; and $R^2$ is hydrogen or methyl.

6. The compound according to claim 1 wherein $R^4$ is naphthyl which is unsubstituted or is substituted by up to three substituents selected from cyano; nitro; $C_{1-6}$alkylsulfonyl; halo; $C_{1-6}$alkoxy; methylenedioxy (—OCH$_2$O—); $C_{1-6}$alkyl; $C_{2-6}$alkenyl; $C_{2-6}$alkynyl; $C_{1-6}$alkyl-carbamoyl; di-$C_{1-6}$alkylcarbamoyl; $C_{1-6}$alkanoyl; $C_{1-6}$alkanoylamino; aminosulfonyl; and cyano$C_{1-6}$alkyl.

7. The compound according to claim 6 wherein $R^4$ is naphthyl which is unsubstituted or is substituted by up to three substituents selected from cyano, methoxy, ethoxy, isopropoxy, fluoro, bromo, chloro, iodo, nitro, cyanomethyl, carboxy, carbamoyl, ethynyl, methyl, ethyl, dimethylcarbamoyl, methylsulfonyl, aminosulfonyl, prop-2-enyl, acetyl and acetylamino.

8. The compound according to claim 6 wherein $R^4$ is naphthyl which is unsubstituted or is substituted by up to two substituents selected from cyano, methoxy, ethyl, fluoro and nitro.

9. The compound according to claim 8 wherein $R^4$ is 3-cyanonaphth-1-yl, 3-cyano-2-methoxynaphth-1-yl, 2,3-dimethoxynaphth-1-yl or 3-cyano-2-ethylnaphth-1-yl.

10. A pharmaceutical composition which comprises a compound according to claim 1; and a pharmaceutically acceptable carrier or diluent.

11. A method of treating a disease condition selected from rheumatoid arthritis, Alzheimer's diseases schizophrenia, oedema, allergic rhinitis, inflammation, pain, gastrointestinal-hypermotility, gastric asthma, gastroesphageal reflux, anxiety, emesis, Huntington's Disease, psychoses, depression, hypertension, migraine and urticaria, which comprises administering to a warm-blooded animal a therapeutically-effective amount of a compound according to claim 1.

* * * * *